United States Patent [19]
Podney

[11] Patent Number: 5,633,583
[45] Date of Patent: May 27, 1997

[54] MAGNETIC TELESCOPE WITH ENHANCED NOISE SUPPRESSION

[75] Inventor: Walter N. Podney, San Diego, Calif.

[73] Assignee: Gas Research Institute, Chicago, Ill.

[21] Appl. No.: 487,418

[22] Filed: Jun. 7, 1995

[51] Int. Cl.⁶ .................. G01N 27/82; G01R 33/035; G01V 3/165
[52] U.S. Cl. .................. 324/241; 324/225; 324/232; 324/233; 324/242; 324/248; 505/843; 505/846
[58] Field of Search .................. 324/329, 225, 324/232, 233, 239–243, 248, 262, 529, 71.2; 505/842–846

[56] References Cited

U.S. PATENT DOCUMENTS

| | | | |
|---|---|---|---|
| 2,939,071 | 5/1960 | Foerster | 324/241 |
| 4,320,341 | 3/1982 | Lutes | 324/248 |
| 4,613,816 | 9/1986 | Zeamer | 324/248 |
| 4,639,675 | 1/1987 | Hinton | 324/334 |
| 4,663,590 | 5/1987 | Gershenson et al. | 324/248 |
| 5,020,538 | 6/1991 | Morgan et al. | 324/248 X |
| 5,087,873 | 2/1992 | Murphy et al. | 324/529 X |
| 5,126,654 | 6/1992 | Murphy et al. | |
| 5,194,812 | 3/1993 | Yokoi | 324/326 |
| 5,293,119 | 3/1994 | Podney | 324/242 |
| 5,311,127 | 5/1994 | Bisiaux | 324/242 X |
| 5,367,259 | 11/1994 | Matsumoto et al. | 324/248 |

OTHER PUBLICATIONS

"Use of a Superconductive Magnetic Gradiometer Near Magnetic Objects," Podney, et al., J. Appl. Phys. 54(6) Jun. 1983, pp. 3544–3553.

"Use of a Superconductive Gradiometer in an Ultrasensitive Electromagnetic Metal Detector," Czipott, et al., IEEE Trans. Magn, MAG–25, 1204–1207, 1989.

"Pulsed Operation of a Superconductive Electromagnetic Gradiometer," Czipott, et al., IEEE Trans. Magn, MAG–27, 1991.

"An Electromagnetic Microscope for Eddy Current Evaluation of Materials," Podney, et al., IEEE Trans. on Magnetics, vol. 27, pp. 3241–3244, Mar. 1991.

"Performance Measurments of a Superconductive Microprobe for Eddy Current Evaluation of Subsurface Flaws," Podney, SQM Technology, Inc. Report Aug. 24, 1992.

*Primary Examiner*—Gerard R. Strecker
*Attorney, Agent, or Firm*—Greer, Burns & Crain, Ltd.

[57] ABSTRACT

A magnetic telescope utilized to detect flaws in underground articles such as underground piping, implements multiple stages in the form of geometric and electronic configurations to enhance noise suppression. The geometric configuration includes a differential configuration of two pair of source coils which generate the magnetic flux, and gradiometers which pick-up the magnetic flux. A superconducting quantum interference device (SQUID) is utilized to detect the magnetic flux. The electronic configuration includes circuitry to adjust the current in the source coil pairs to minimize the signal seen by the SQUID when no underground article is present. The electronic configuration also includes feedback circuitry to feed back magnetic flux to the SQUID based on the signal detected by the SQUID. Combining the geometric and electronic configurations provides enhanced noise suppression so that the SQUID is capable of detecting smaller flaws in the underground piping for the same amount of source magnetic flux.

11 Claims, 8 Drawing Sheets

MAGNETIC TELESCOPE WITH ENHANCED NOISE SUPPRESSION

FIELD OF THE INVENTION

The invention relates generally to magnetic telescopes utilized for locating flaws in underground piping, and more particularly to noise suppression techniques implemented in such magnetic telescopes.

BACKGROUND OF THE INVENTION

The use of underground pipes to carry fluids and gasses is prevalent throughout the world. Typically, these pipes are utilized to carry water, natural gas, etc. During installation of the pipes, flaws may occur in the pipe. One common flaw, for example, that would be seen as an installation flaw would be a bad weld between two connected pipes.

Not only do installation errors occur which lead to flaws in the pipe, but the pipe can develop flaws over the period of time it is in the ground. For example, a significant portion of the piping used for underground fluid transfer is comprised of a metal alloy. When exposed to damp conditions, the metal alloy has a tendency to corrode at certain locations throughout the pipe. If the pipe corrodes all the way through the wall of the pipe, the fluid being transferred will eventually escape. In the case of natural gas being transferred by a pipe having an entire wall corroded, a dangerous situation (for example, an explosion) may result.

Not only will the pipe have a tendency to corrode, but the pipe may also experience cracks. These cracks may be due to, inter alia, shifting of the ground where the pipe is located or a significant amount of weight placed on the ground directly above the location of the pipe. While the latter condition is less of a problem when there is high overburden (i.e., the amount of soil between the ground surface and the pipe), significant weights may still create very small cracks throughout the length of the pipe. Even these small cracks may present the dangerous situation described above.

Prior art methods to determine the location and/or magnitude of a point of corrosion or a crack in underground piping exist. For example, in U.S. Pat. No. 5,087,873 to Murphy et al., a sinusoidal current is introduced into the pipe and magnetic sensors placed along the length of the pipe detect the resulting sinusoidal magnetic fields emanating at various locations of the pipe. Based on the detected magnetic fields, corrosion points along the length of the pipe can be determined. This method is impractical, however, since access to the pipe to apply the sinusoidal current is required. Also, a plurality of magnetic sensors must be located throughout the length of the pipe. Consequently, this method is implementation and cost prohibitive.

Other methods to determine the location and magnitude of a corrosion point or a crack in underground piping exist. For example, as described in U.S. Pat. No. 4,613,816 to Zeamer, a magnetic probe capable of detecting the location of a magnetic anomaly is implemented. A superconducting quantum interference device (SQUID) is coupled to gradiometer coils and a magnetometer, and detects the magnetic fields sensed by the magnetometer and the gradiometer coils to determine the intensities, directions and gradients of the article under consideration. A SQUID is a relatively new technology for inspection of underground piping such as gas transmission lines. SQUIDs are described in U.S. Pat. No. 5,293,119 to Podney, which is incorporated herein by reference in its entirety. SQUIDs provide unprecedented sensitivity at ultra low frequencies (~10 Hertz), to enable inspection of buried pipelines from the surface. Their magnetic flux resolution of $10^{-6}$ $\Phi_o/\sqrt{Hz}$ enables a magnetic telescope to measure leakage of magnetic flux from pipeline flaws through a 2 m overburden, where a quantum of magnetic flux, $\Phi_o$, is $2.07 \times 10^{-15}$ Webers. The detection of small flaws, however, is severely limited by physical properties of the magnetic telescope itself.

For example, the magnetic telescope typically is the source of the magnetic field which is detected by the SQUID. The source, however, significantly contributes to the amount of interference seen by the SQUID. In order for the SQUID to achieve the sensitivities that it is capable of, the SQUID must be in as "quiet" an environment as possible. In other words, noise suppression at the location of the gradiometers and the SQUIDs must be optimized. By optimizing the noise suppression at the location of the gradiometers and the SQUIDs, smaller corrosion patches or cracks may be detected for the same amount of source energy which is output by the magnetic telescope. This in turn has the advantage of locating corrosion early, or cracks while they are still small, thus substantially mitigating the dangerous effects that such corrosion or cracks may eventually produce.

Thus, a need exists for a magnetic telescope which overcomes the interference presented by its own source by enhancing noise suppression so that the sensitivity of a SQUID, as used therein, is increased.

It is therefore an object of the present invention to provide improved noise suppression in a magnetic telescope in accordance with the invention.

It is another object of the present invention to provide improved noise suppression by implementing a geometric and electronic configuration in a magnetic telescope.

A related object of the present invention is to provide a differential source coil and gradiometer geometric configuration to enhance noise suppression in a magnetic telescope.

Still another related object of the present invention is to provide an electronic configuration by adjusting the currents in the source coils and balancing the magnetic flux in the gradiometers.

Another object of the present invention is to provide an improved dewar in which the magnetic telescope resides during use.

A related object of the present invention is to provide an improved dewar which has improved cryogenic efficiency with a compact, small, lightweight design.

SUMMARY OF THE INVENTION

In keeping with one aspect of this invention, a magnetic telescope utilized to detect flaws in underground articles, such as underground piping, implements multiple stages in the form of geometric and electronic configurations to enhance noise suppression caused by its source of magnetic flux. Buried ordnance, underground oil tanks and other ferrous metal objects can also be detected. The geometric configuration includes a differential configuration of source coils which generate the magnetic flux, and gradiometers which pick-up the magnetic flux. A superconducting quantum interference device (SQUID) is utilized to detect the magnetic flux. The electronic configuration includes circuitry to adjust the current in the source coils to minimize the signal seen by the SQUID when no underground article is present. The electronic configuration also includes feedback circuitry to feed back magnetic flux to the SQUID based on the signal detected by the SQUID. Combining the geometric and electronic configurations provides enhanced noise suppression so that the SQUID is capable of detecting smaller flaws in the underground piping for the same amount of source magnetic flux.

Stated generally, the magnetic telescope includes a means, which is in a differential configuration, for transmitting a first signal. The magnetic telescope also includes a means, substantially located within the differential configuration of the means for transmitting magnetic flux, for receiving a second signal induced by the first signal, but having noise thereon. The means for receiving is also in a differential configuration. The magnetic telescope further includes a means for electronically balancing predetermined aspects of the magnetic telescope.

In the preferred embodiment, the means for transmitting a first signal has at least two source coil pairs. Each pair includes an outer source coil which substantially encompasses an inner source coil. The two source coil pairs are spaced apart along a common axis. The two source coils of each pair carry currents which are substantially equal in magnitude and opposite in direction. Also in the preferred embodiment, the means for receiving is substantially located within the inner coil.

Likewise in the preferred embodiment, the means for electronically balancing predetermined aspects of the magnetic telescope adjust the currents to maximize suppression of the noise in the second signal. The means for electronically balancing predetermined aspects of the magnetic telescope also adjusts the current of the second signal to maximize suppression of the noise in the second signal. The adjustment is accomplished with the aid of a feedback current related to the noise of the second signal. When the adjustments for noise suppression are made, flaws can be detected in the usual manner.

The magnetic telescope described above is maintained at cryogenic temperatures by a compact dewar. The compact dewar includes a first half having first and second walls, where the first and second walls are mounted to a first end to form a double-walled bucket configuration. The compact dewar also includes a second half having third and fourth walls, where the third and fourth walls are mounted to a second end to also form a double-walled bucket configuration. The first and second walls are offset from the third and fourth walls such that the first and second walls mate with the third and fourth walls when the first and second ends are brought towards one another.

In the preferred embodiment, at least the first, second and third walls of the compact dewar include at least one crenelated surface. The crenelated surfaces form, during mating of the first half with the second half, a spiral groove which allows vapor from a liquid helium reservoir to escape. The compact dewar has improved cryogenic efficiency (i.e., reduce liquid helium boiloff) with a compact, lightweight design.

BRIEF DESCRIPTION OF THE DRAWINGS

These and other objects will become apparent upon reading the following detailed description of the preferred embodiment of the present invention, while referring to the attached drawings.

DETAILED DESCRIPTION OF A PREFERRED EMBODIMENT

Figure 1:
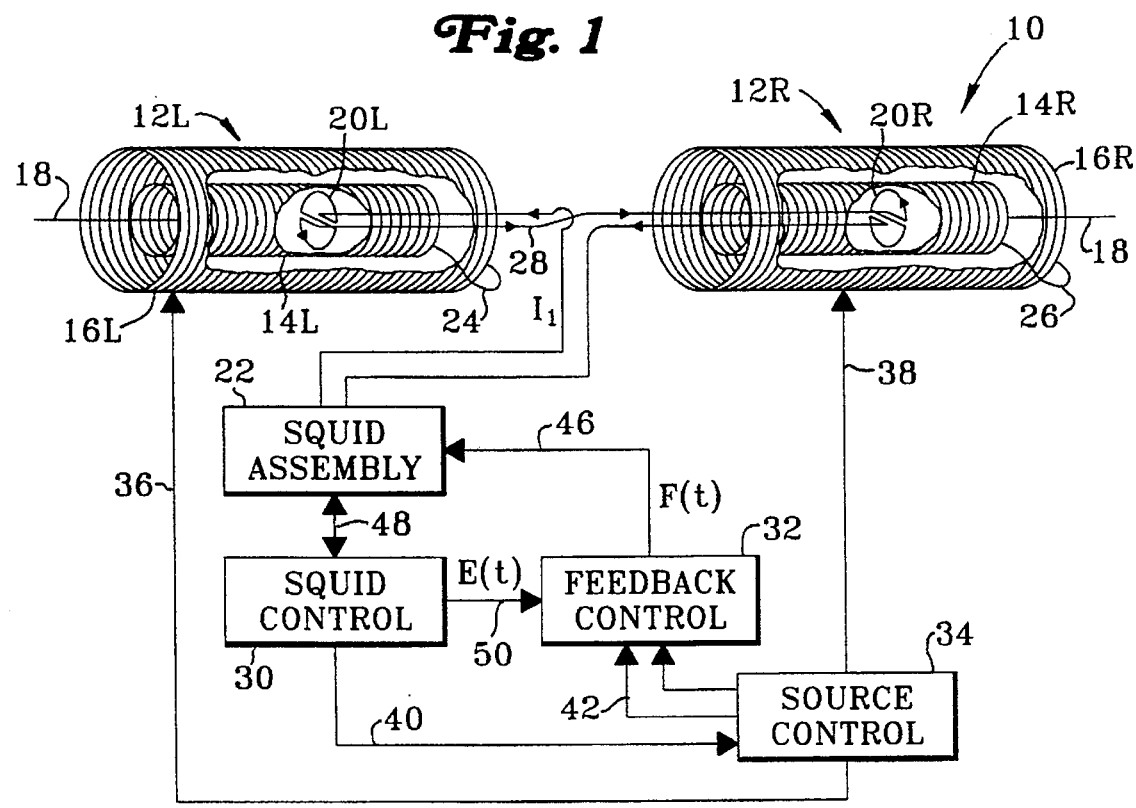
FIG. 1 generally depicts a schematic diagram of a magnetic telescope having enhanced noise suppression in accordance with the invention.

A magnetic telescope having enhanced noise suppression in accordance with the invention is generally designated 10 in FIG. 1. As shown in FIG. 1, the apparatus 10 includes a first pair of source coils 12L which includes a differential configuration of an inner solenoid 14L connected in series with an outer solenoid 16L. The apparatus 10 also has a second pair of source coils 12R which includes an inner solenoid 14R connected in series in a differential configuration with an outer solenoid 16R. The coil pairs 12L and 12R are spaced coaxially along an axis 18. Magnetic moments produced by each source coil pair 12L, 12R add. Differential gradiometers 20L and 20R, which are likewise aligned coaxially along the axis 18, are located in the center of each source coil pair 12L and 12R, respectively, and connect oppositely in series to a SQUID assembly 22. The differential gradiometers 20 are designed having a predetermined radius $r_r$, which has a significant effect on their sensitivity. A wire 24 connects the coils 14L and 16L, while a wire 26 connects the coils 14L and 14R. The gradiometers 20L, 20R are connected by wire 28.

A SQUID control block 30 controls the operation of the SQUID assembly 22. Oxford Instruments in England makes a suitable SQUID control block. A feedback control block 32 feeds magnetic flux back to the gradiometers 20L, 20R to null interfering flux produced by the source coils 12L, 12R. A source control block 34 provides a reference to the feedback control block 32 and also supplies the drive current for the source coils 12. The drive current for the coils 14L, 16L is supplied via a line 36, while the drive current for the coils 14L, 16L is supplied via a line 38.

Output from the SQUID control block 30 is input into the source control block 34 via a line 40. The source control block 34 has outputs which are input to the feedback control block 32 via lines 42 and 44. A feedback signal F(t) is input into the SQUID assembly 22 from the feedback control block 32 via a line 46. The SQUID assembly 22 is also coupled to the SQUID control block 30 via a line 48, while an error signal E(t) is input into the feedback control block 32 from the SQUID control block 30 via a line 50.

To better understand the magnetic telescope 10 having enhanced noise suppression in accordance with the invention, the physical characteristics and performance expectations of the magnetic telescope 10 will be reviewed.

Figure 2:
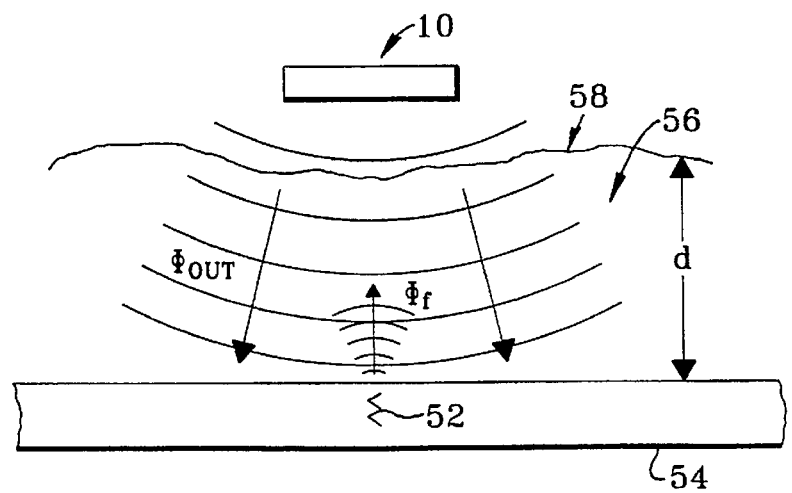
FIG. 2 generally depicts a typical implementation of the magnetic telescope of FIG. 1 in accordance with the invention.

A typical implementation of the magnetic telescope 10 in accordance with the invention is depicted in FIG. 2. The performance expectations of the magnetic telescope 10, in general, follow from dipole expressions for both the magnetic field $H_{OUT}$ of the source coils 12L, 12R and for the magnetic flux $\Phi_F$ leaking from a flaw 52 in an underground pipe 54. As shown in FIG. 2, a pipe 54 is located in an overburden 56 beneath the ground surface 58 by a distance d. The source coils of the magnetic telescope 10 illuminate the pipe 54 by channeling magnetic flux $\Phi_{OUT}$ into the pipe 54. By illuminating the pipe 54, the magnetization of the pipe changes. Consequently, a flaw 52 in the pipe 54 will cause magnetic flux $\Phi_f$ to leak from the pipe. As such, the magnetic flux $\Phi_f$ exiting the flaw 52 will appear to come from a magnetic dipole located at the flaw.

The dipole moment, $m_f$, resulting from illuminating a flaw 52 of effective radius $r_f$ a magnetic field $\vec{H}_{OUT}$ is given by $$m_f = -2\pi r^3 \vec{H}_{OUT} \quad [1]$$

The magnitude of the magnetic field $H_{OUT}$ at the pipe 54 located a distance d from a solenoidal source coil 12L, or 12R (FIG. 1) of moment $m_s$, is given by $$H_{OUT} \cong \frac{m_s}{4\Pi d^3} \quad [2]$$

Substituting $H_{OUT}$ of equation [2] into equation [1] yields $$m_f \cong \frac{m_s}{2} \left( \frac{r_f}{d} \right)^3 \quad [3]$$

As seen from equation [3], a flaw 52 having an effective radius $r_f$=1 centimeter (cm) at a distance d=1 meter (m) results in the flaw moment $m_f$ being approximately one millionth of the source moment $m_s$. Stated algebraically, $m_f/m_s \cong 0.5 \times 10^{-6}$.

The approximate expression for the net magnetic flux, $\Phi_r$, in a planar gradiometer, wound with $N_r$ turns on a diameter $2r_r$ from a gradient of magnitude $g_f$ is given by $$\Phi_r \cong \frac{4}{3} N_r r_r^3 g_f \quad [4]$$

where the expression $$g_f = \frac{3\mu_o m_f}{4\pi d^4} \quad [5]$$

gives the gradient magnitude $g_f$ at the gradiometers from a dipole of moment $m_f$ at a distance d. In equation [5], the constant $\mu_o$ is equal to $4\pi \times 10^{-7}$ Henrys/meter (H/m). Consequently, $$\Phi_r \cong \left( \frac{\mu_o m_f}{\Pi} \right) \frac{N_r}{r_r} \left( \frac{r_r}{d} \right)^4 \quad [6]$$

so a flaw 52 of unit moment (1 Ampere×m²) at a distance d=1 m gives a net magnetic flux $\Phi_f$ of $4 \times 10^{-13}$ Webers, or about 100 flux quanta, in a gradiometer of $N_r$=1 with a radius $r_r$=1 cm. A quantum of magnetic flux, $\Phi_o$, is equal to $2.07 \times 10^{-15}$ Webers.

Figure 3:
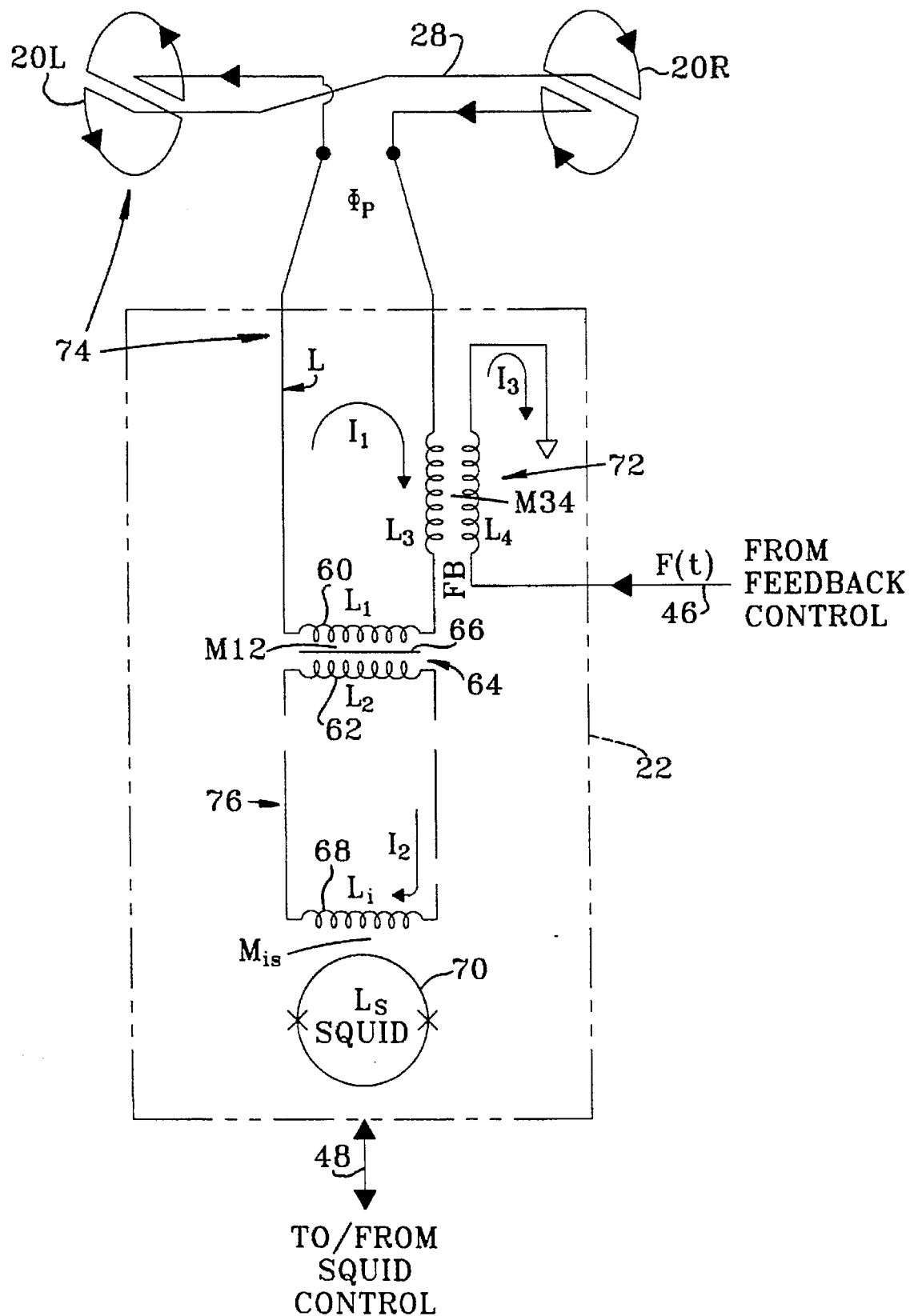
FIG. 3 generally depicts a detailed view of the SQUID assembly of FIG. 1.

A detailed view of the SQUID assembly of FIG. 1 is depicted in FIG. 3. As shown in FIG. 3, the gradiometers 20L, 20R couple magnetic flux to the SQUID assembly 22.

The gradiometers 20L, 20R connect oppositely in series and pickup magnetic flux $\Phi_p$. Transfer of the magnetic flux $\Phi_p$ from a primary winding 60 to a secondary winding 62 is accomplished through a transformer 64, which filters interference at radio frequencies (RF) by using a copper shield 66 between windings. The secondary winding 62 of the transformer 64 has a mutual inductance of $M_{12}$ to the primary winding 60 and connects to an input winding 68 which has a self inductance of $L_i$. The input winding 68 inductively couples magnetic flux, $\Phi_s$, to the SQUID 70 which has a self inductance of $L_s$. A feedback transformer 72 having a mutual inductance of $M_{34}$ couples magnetic flux into the gradiometers 20L, 20R to null flux oscillations at the frequency of the source coils 12L, 12R.

Because the circuits in FIG. 3 are superconducting, the magnetic flux within them is constant. The expression for conservation of flux in a primary circuit 74 of self inductance L can be given by $$L I_1 + M_{12} I_2 + M_{34} I_3 + \Phi_p = 0 \quad [7]$$

where $I_1$ is the supercurrent in the primary circuit 74, $I_2$ is the supercurrent in a secondary circuit 76, and $I_3$ is an external current in the feedback transformer 72. The relation $$M_{12} I_1 + (L_2 + L_i) I_2 = 0 \quad [8]$$

expresses conservation of flux in the secondary circuit 76 having a self inductance of $L_2 + L_i$. The SQUID 70 is effectively an open circuit, and thus returns no flux. The flux transfers to the SQUID 70 through mutual inductance of $M_{is}$, so $\Phi_S = M_{is} I_2$.

Combining equations [7] and [8] gives the currents $$I_1 = \frac{-(L_2 + L_i)(M_{34} I_3 + \Phi_p)}{\Delta} \quad [9]$$

and $$I_2 = \frac{M_{12}(M_{34} I_3 + \Phi_p)}{\Delta} \quad [10]$$

where $\Delta = L(L_2 + L_i) - (M_{12})^2$ and $\Phi_r = M_{34} I_3 + \Phi_p$ is the total flux coupled to the gradiometers 20L, 20R. Consequently, the expression for the ratio of flux transferred to the SQUID 70 to total flux coupled to the gradiometers 20L, 20R is given by $$\frac{\Phi_S}{\Phi_r} = \frac{M_{is} M_{12}}{L(L_2 + L_i) - (M_{12})^2} \quad [11]$$

Equation [11], expressing efficiency of flux transfer to a SQUID 70, shows that the ratio of mutual inductance $M_{is}$ to the inductance L of the gradiometers 20L, 20R sets the order of magnitude of the coefficient of flux transfer; namely $\Phi_S/\Phi_r \sim M_{is}/L$. Since the mutual inductance $M_{is}$ of the input winding 68 and the SQUID 70 is typically a few nanoHenrys (nH, where 1 nH=$1 \times 10^{-9}$ H), and the inductance L of the gradiometers 20L, 20R is typically a few microHenrys (μH, where 1 μH=$1 \times 10^{-6}$ H), the efficiency of flux transfer from the gradiometers 20L, 20R to the SQUID 70 is approximately a few tenths of a percent.

Since the gradiometers 20L, 20R transfer about one thousandth of their flux to the SQUID 70, a flaw 52 of unit moment gives a flux of approximately $0.2\Phi_o$. Because the resolution of the SQUID 70 is about $10^{-6}$ $\Phi_o/\sqrt{Hz}$ or $10^{-21}$ Webers/$\sqrt{Hz}$, the SQUID can resolve a flaw moment $m_f$ of approximately $5 \times 10^{-6}$ A m² (Amperes×square meters).

Figure 4:
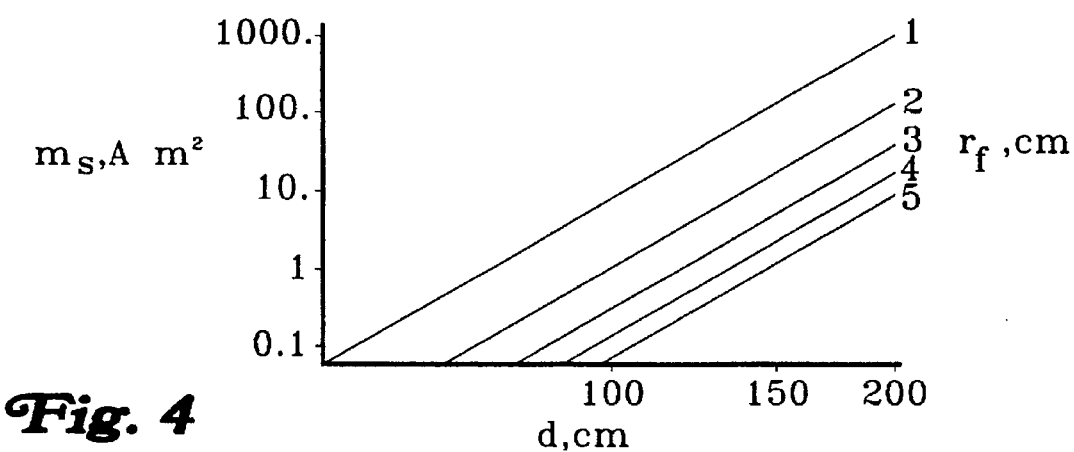
FIG. 4 generally depicts a graph of source moments, $m_s$, required to illuminate and detect a flaw of 1, 2, 3, 4, and 5 cm in radius at distances d from 50 to 200 cm.

A graph of source moments, $m_s$, required to illuminate and detect a flaw 52 (FIG. 2) of 1, 2, 3, 4, and 5 cm in radius at distance d from 50 to 200 cm is depicted in FIG. 4. The graph of FIG. 4 assumes that gradiometers 20 having $N_r=1$ and a radius $r_r=1$ cm are utilized. As is clear from FIG. 4, the required source moments $m_s$ extend to 1,000 A m², which is the largest practical source moment achievable with a compact magnetic telescope. To achieve 1,000 A m², a source coil having 25,000 turns and 10 cm in diameter carrying 5 A would be required. The values depicted in FIG. 4 give the best achievable performance for an effective flux resolution of $10^{-3}$ $\Phi_o/\sqrt{Hz}$ at the gradiometers 20. The values show that centimeter size flaws give reasonable signals at distances d of a meter or two. Ambient noise in the carrier bandwidth and interference from the source coils 12 will degrade performance, however.

Source interference, in the form of magnetic flux $\Phi_r$, must also be considered in the design of the magnetic telescope 10. The source interference is the magnetic flux $\Phi_r$ from the source coils 12L, 12R which interferes with the gradiometers 20L, 20R multiplied by a suppression factor $\beta$.

The source interference can be expressed as $$\Phi_r = B_{ns} N_r \pi r_r^2 \beta \quad [12]$$

where $B_{ns}$ is the magnetic flux density from the source coils 12L, 12R, normal to the gradiometers 20L, 20R. In the interior of a long solenoid, the magnetic flux density from the source coils 12L, 12R is $\mu_o m_s/V_s$, where $m_s$ is the solenoid moment and $V_s$ is the solenoid volume. Consequently, the interference in the coaxial gradiometers 20L, 20R from a solenoid of moment $m_s$, length $L_s$, and radius $r_s$ is given by the expression $$\Phi_I = \left( \frac{\mu_o m_s}{L_s \Pi r_s^2} \right) N_r \Pi r_r^2 \beta \quad [13]$$

Now using equation [6], the expression for the ratio of signal flux from a flaw 52 to interfering flux from the source coils is $$\frac{\Phi_r}{\Phi_I} = \frac{1}{\beta} \left( \frac{L_s}{2\Pi r_s} \right) \left( \frac{r_s}{r_r} \right)^3 \left( \frac{r_f}{d} \right)^3 \left( \frac{r_r}{d} \right)^4 \quad [14]$$

The suppression factor $\beta$ is expressed by the illumination factor $(r_r/d)^3$, and the decrease in signal with distance from the gradiometers, expressed by the gradient factor $(r_r/d)^4$. For a flaw 52 having an effective radius of 1 cm at a distance d=1 m, a suppression factor of $1.25\times10^{-12}$ gives a flux ratio of unity in gradiometers which have a radius $r_r=1$ cm, coaxial with the source coils which are 10 cm in diameter and $10\pi$ cm long.

Figure 5:
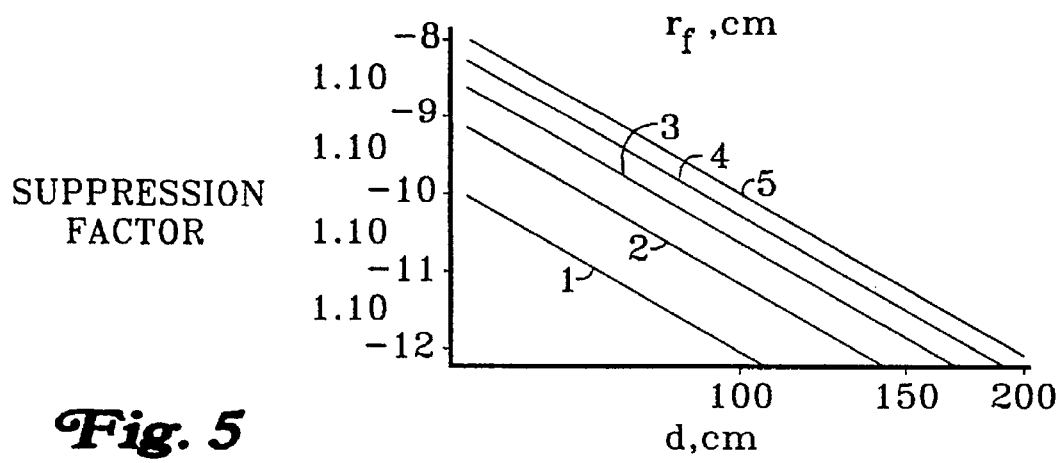
FIG. 5 generally depicts a graph of noise suppression factors vs. overburden distances d for various radii rf of a flaw.

A graph of noise suppression factors vs. overburden distances d for various radii of the flaw 52 is depicted in FIG. 5. Specifically, FIG. 5 gives noise suppression factors required to achieve a unit flux ratio in the gradiometers which have a radius $r_r=1$ cm and which are coaxial with the source coils which are themselves 10 cm in diameter and $10\pi$ cm long. The radii of the flaw 52 vary from 1, 2, 3, 4, and 5 cm at distances d of 50 to 200 cm. As is clear from FIG. 5, the noise suppression factors realistically extend to a lower limit of $10^{-12}$.

Comparison of FIG. 4 and FIG. 5 shows that achievable noise suppression factors limit performance of the magnetic telescope 10. Noise suppression of $10^{-12}$, for example, gives a detection distance d of 1 m for a 1 cm flaw 52, as shown in FIG. 5. Referring now to FIG. 4, a corresponding source moment $m_s$ of 10 A m² is required. Although a source moment $m_s$ of 100 A m² is practical, and gives a detection range of 140 cm (1.4 m), use of such a high level source moment would require an impracticably small noise suppression of $10^{-13}$. As such, for a compact magnetic telescope, a source moment $m_s$ of 10 A m² coupled to gradiometers which can detect a 1 cm flaw with a 1 m overburden requires a noise suppression of $10^{-12}$.

The magnetic telescope 10 in accordance with the invention achieves a noise suppression of $10^{-12}$. The magnetic telescope 10 implements multiple stages, where each stage is capable of attaining a noise suppression of $10^{-3}$. As such, four stages of noise suppression are implemented to yield a total noise suppression of $10^{-12}$. Two stages of noise suppression use geometric configurations such as differential positioning of the source coils 12L, 12R and the gradiometers 20L, 12R, while the remaining two stages of noise suppression use electronic balancing of the source coils 12L, 12R and the gradiometers 20L, 20R.

Referring back to FIG. 1, the differential configuration of the source coils 12L, 12R provides the first stage of noise suppression in accordance with the invention. The source coils 12L, 12R are in a differential configuration which include the inner coaxial solenoids 14L, 14R and the outer coaxial solenoids 16L, 16R, respectively. Both the inner solenoid and the outer solenoid of each pair carry the same electric current in windings having the same number of turns per unit length. The central magnetic field of the inner solenoid 14 nulls the magnetic field of the outer solenoid 16, resulting in a vanishingly small magnetic field on the inside of the source coil 12, near the axis 18.

Far outside the source coils 12L, 12R, the magnetic field originates from a dipole with a net moment proportional to the difference in volume of the inner solenoids 14L, 14R and the outer solenoids 16L, 16R. The magnetic moment, m, of a long solenoid is the product of its central magnetic field, $H_c$, and its volume, V; $m = H_c V$. The central magnetic field is the product of current, I, in a winding of n turns in unit length; $H_c = nI$. The fractional reduction in moment m of the outer solenoid is $\Delta V/V_o$, where $V_o$ is the volume of the outer solenoid and $\Delta V$ is the differential volume between the inner solenoid and the outer solenoid. A 20% reduction in moment m can result in a thousandfold suppression of interference from the source coil.

Still referring to FIG. 1, differential gradiometers 20L, 20R provide the second stage of noise suppression in accordance with the invention. The gradiometers 20L, 20R include a coplanar pair of oppositely wound semicircles, with a common diameter. A perfect winding (i.e., a winding with perfect semicircles) would give zero response to a magnetic field that is symmetric about the axis 18 of the source coils 12L, 12R, which would result in infinite noise suppression (i.e., no noise). However, winding imperfections typically limit the suppression of axially symmetric fields to approximately $10^{-4}$.

The expression for the magnetic flux in an imperfectly wound planar gradiometer of radius $r_r$, coming from a magnetic flux density $\vec{B}_o$ and its gradient $\hat{x} \cdot \vec{\nabla}(\hat{n} \cdot \vec{B})_o$ at the center of the gradiometer is given by $$\Phi_r = \tfrac{1}{3} r_r^3 [\hat{x} \cdot \vec{\nabla}(\hat{n} \cdot \vec{B})_o] + \sigma \delta \vec{A} \cdot \vec{B}_o \quad [15]$$

An imperfect winding gives an imbalance in area, $\sigma \delta \vec{A}$, between the semicircles that then pick up flux directly from $\vec{B}_o$ as well as its gradient.

For a magnetic dipole of moment $m_f$ at distance d from a flaw 52, equation [15] gives the relation $$\Phi_r \cong \frac{\mu_o m_f}{4\Pi d^3} (\Pi r_r^2) \left[ \frac{4r_r}{\Pi d} + \left( \frac{\delta r_r}{r_r} \right)^2 \right] \quad [16]$$

which is the expression of the flux in a planar gradiometer with an effective radial error $\delta r_r$ in its winding. A radial error of 1% gives a suppression of $10^{-4}$. In the preferred embodiment, two such gradiometers are connected in series to form a first-order, off-diagonal gradiometer.

Balancing the differential configuration of the source coils 12 is the third stage of noise suppression in accordance with the invention. Referring to FIG. 1, the currents produced by the source control block 34 and output to the left end solenoid pair 12L over the line 36 and to the right-hand solenoid pair 12R over the line 38 are adjusted so that a minimal signal is seen by the SQUID 70 when no pipe 54 is present. A signal from the SQUID 70 is input to the source control block 34 over the line 40 to aid in the current adjustment. By minimizing the signal seen by the SQUID 70 using the electronic balancing of currents of the source coils 12L and 12R, an additional $10^{-3}$ noise suppression is realized.

Harmonics of the source current frequency can limit electronic performance. Instead of giving interference or noise at the drive frequency, they can exceed the dynamic range of the SQUID 70 by adding energy at high frequencies. The differential configuration of the source coils 12L, 12R and use of the differential gradiometers 20L, 20R can be used to suppress the harmonics by a factor of $10^{-6}$. Together with the $10^{-3}$ suppression obtained by the balancing of the currents of the source coils 12L and 12R, the effects of the harmonics can be effectively eliminated.

Figure 6:
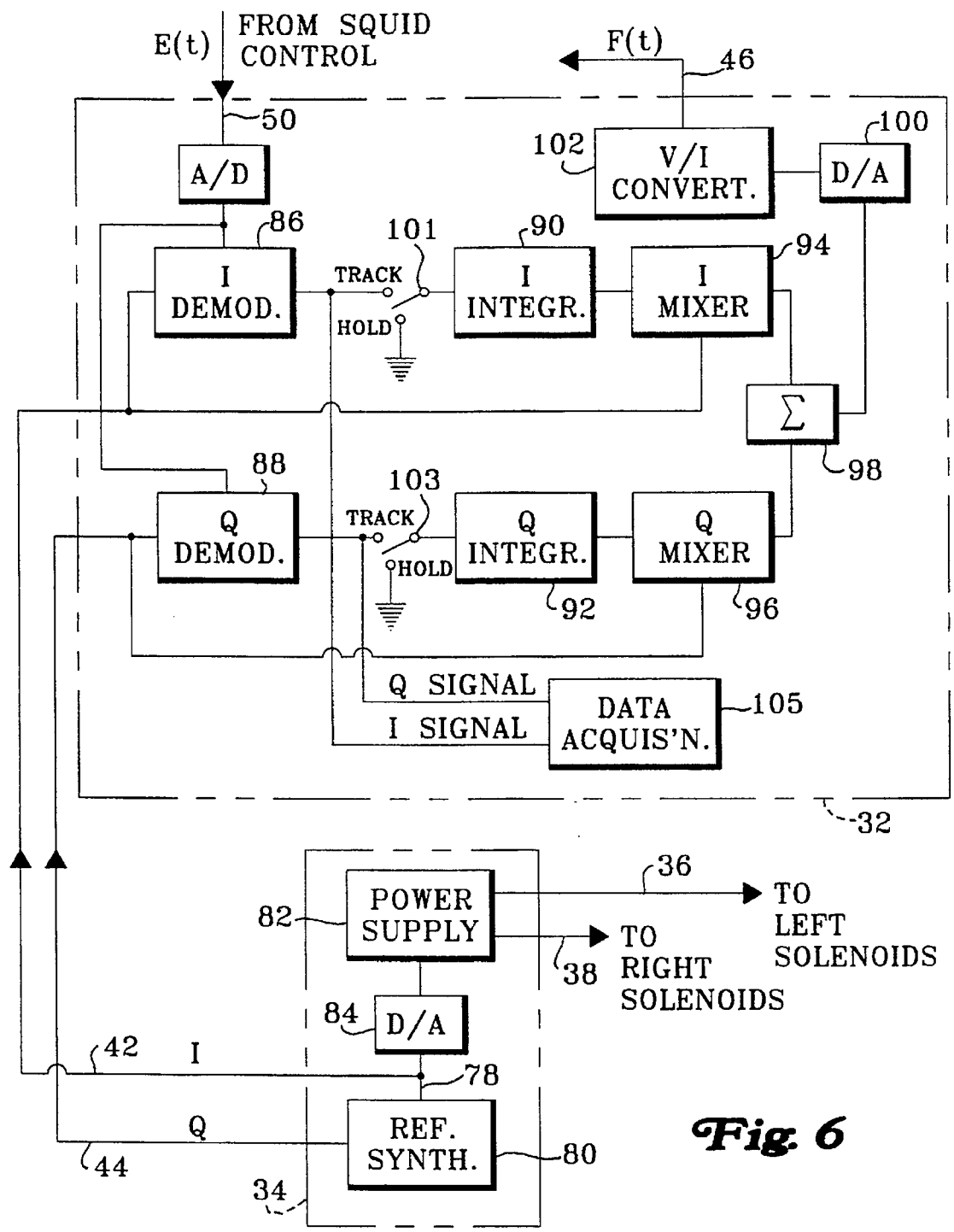
FIG. 6 generally depicts a block diagram of the circuitry for the feedback control block and the source control block of FIG. 1.

The use of current fed back to the gradiometers 20L, 20R to null residual interference at the SQUID 70 is the fourth and final stage of noise suppression. A block diagram of circuitry for the feedback control block 32 and the source control block 34 is depicted in FIG. 6. The circuitry is utilized to feed back magnetic flux to the gradiometers 20L, 20R to null interfering flux from the source coils 12L, 12R.

Referring to the source control block 34, a sinusoidal signal 78 from a reference synthesizer 80 provides a frequency and phase reference for a power supply 82 that drives the source coils 12L, 12R and the circuitry of the feedback control block 32. In the preferred embodiment, the reference synthesizer 80 is a digital synthesizer which outputs a digital signal which represents a sinusoidal signal 78 at a frequency of 8 Hertz (Hz). Other frequencies of the sinusoidal signal are contemplated, however. A digital-to-analog (D/A) converter 84 converts the digital sinusoidal signal 78 to an analog signal for use by the power supply 82.

Referring to the feedback control block 32, an I demodulator 86 (where I represents "in-phase") and a Q demodulator 88 (where Q represents "out-of-phase" or "quadrature phase") each give amplitude information of the I and Q components of the error signal E(t). The I reference is input into the feedback control block 32 via the line 42, while the Q reference is input into the feedback control block 32 via the line 44. Continuing, the signals exiting the I demodulator 86 and the Q demodulator 88 respectively enter an I integrator 90 and a Q integrator 92.

The output of the I integrator 90 and the Q integrator 92 are multiplied by their corresponding reference signals I and Q (input via the lines 42 and 44, respectively) in an I mixer 94 and a Q mixer 96. The output of the I mixer 94 and the Q mixer 96 are summed at a summing node 98. In the preferred embodiment, the summing node 98 performs a digital summation of the outputs of the I mixer 94 and the Q mixer 96. The digital summation exiting the summing node 98 is converted to an analog signal by a digital-to-analog (D/A) converter 100, and is then converted from a voltage to a current by the voltage-to-current (V/I) converter 102.

The signal on the line 46 exiting the V/I converter 102 is a feedback signal F(t). The feedback signal F(t) is input into the SQUID assembly 22 via the line 46. The current of the feedback signal F(t) is the current $I_3$ depicted in FIG. 3. The current $I_3$ is opposite in phase to the interfering flux produced by the source coils 12. Flux coupled to the gradiometers 20 from the feedback control block 32 via the feedback transformer 72 nulls any interfering flux produced by the source coils 12. The SQUID 70 then produces the residual difference in flux, which is provided to the feedback control block 32 in the form of an error signal E(t). The error signal E(t) from the SQUID 70 enters the feedback control block 32 via the line 50 shown in FIG. 1 and FIG. 6, and is used by the I demodulator 86 and the Q demodulator 88 to produce a refined value of the current $I_3$. The process to null the interference is then repeated until the SQUID 70 detects a minimal amount of interference.

During the noise suppression process, two switches 101, 103 are placed in the "track" position in FIG. 6. When the noise suppression process is completed, the switches 101, 103 are moved to the "hold" position, and detected flaws or other discontinuities are then identified by known data acquisition equipment 105. Other ferrous metal objects such as buried, unexploded weapons, underground tanks and the like can also be detected.

The error signal, E(t), and the interfering flux, $\Phi(t)$, both have orthogonal components, $E_I(t)$, $E_Q(t)$, $\Phi_1(t)$ and $\Phi_2(t)$ which are, respectively, in-phase and quadrature with the reference signal 78 from the reference synthesizer 80. The I demodulator 86 and the Q demodulator 88 extract the components $E_I(t)$, $E_Q(t)$ from the error signal E(t). Orthogonal components, $F_I(t)$ and $F_Q(t)$, of the feedback signal, F(t), are integrals of the components of the error signal E(t), and can be expressed as $$F_i(t) = v \int_0^t E_i(\tau) d\tau \quad [17]$$

where $v$ is a time constant scale factor. The difference between the feedback and the interfering fluxes gives the error signal E(t), thus $$E_i(t) = \Phi_i(t) - v \int_0^t E_i(\tau) d\tau \quad [18]$$

Substituting yields $$E_i(t) = \Phi_i(t) - v \int_0^t \Phi_i(\tau) e^{-v(t-\tau)} d\tau \quad [19]$$

For interference varying slowly over a decay time of the exponential kernel, $e^{-vt}$, $$E_i(t) \cong \Phi_i(t) - v\Phi_i(t) \int_0^t e^{-v(t-\tau)} d\tau \cong \Phi_i(t) e^{-vt} \quad [20]$$

so the error vanishes exponentially with the time constant $v$.

Figure 7:
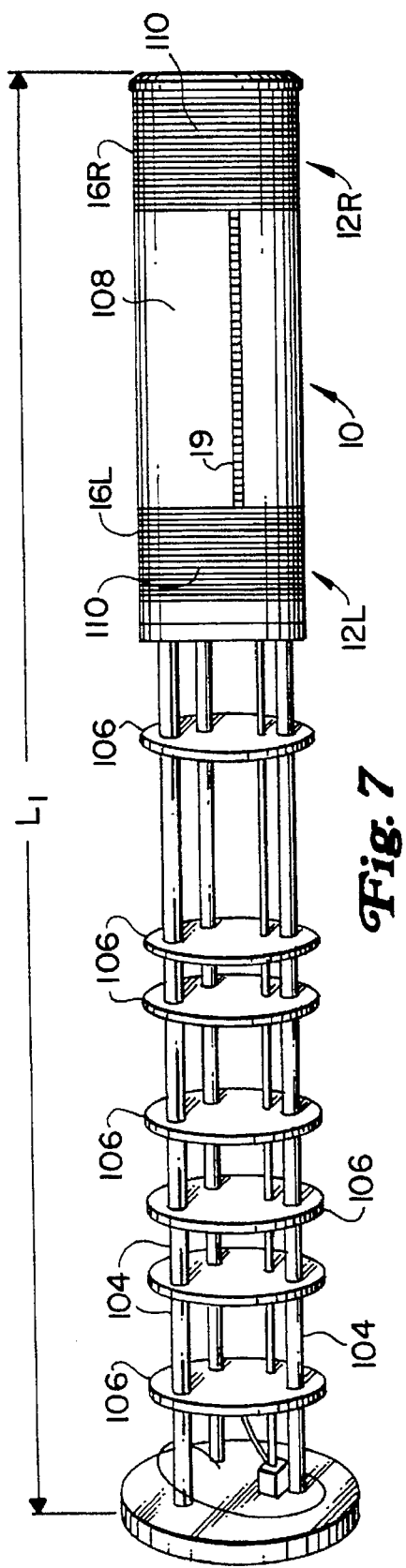
FIG. 7 generally depicts an assembled magnetic telescope made in accordance with the invention.

An assembled magnetic telescope 10 in accordance with the invention is depicted in FIG. 7. The magnetic telescope 10 includes a strong, rigid assembly of G-10 fiberglass tubes 104 and baffles 106. A G-10 cylinder 108 supports the source coils 12L, 12R. FIG. 7 only depicts the outer solenoids 16L, 16R; the inner solenoids cannot be seen in FIG. 7. Each of the outer solenoids 16L, 16R consists of 500 turns of superconducting wire 110, resulting in 1000 turns of superconducting wire total. Each outer solenoid individually produces a magnetic field of 11±0.7 mT/A at its center, resulting in a total magnetic moment of 15,305 A m$^2$ per ampere flowing in the outer solenoids 16L, 16R. Each inner solenoid individually produces the same magnetic field of 11±0.7 mT/A at its center, but resulting in a total magnetic moment of 1,875 A m$^2$ per ampere flowing in the inner solenoids 14L, 14R.

The superconducting wire has a single-filament Niobium Titanium (NbTi) alloy core which is 76 μm in diameter, and is surrounded by copper cladding to result in a diameter of 127 μm. Formvar insulation also covers the superconducting wire 110, resulting in an overall diameter of 142 μm. String made of Kevlar fibers is wound and epoxied around the outer solenoids to protect the outer solenoids from damage. Kevlar is a trademark of DuPont du Nemours Company.

Figure 8:
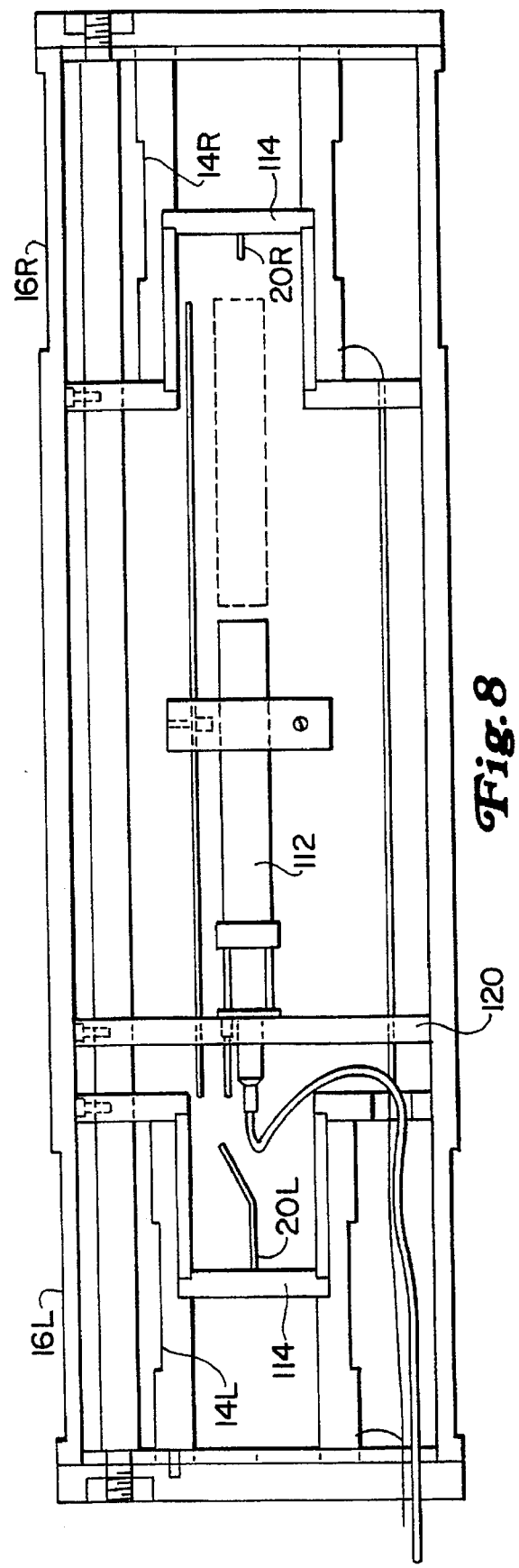
FIG. 8 generally depicts the interior section of the magnetic telescope of FIG. 7.

The interior section of a magnetic telescope 10 is shown in FIG. 8. The SQUID assembly is placed inside a superconductive Niobium (Nb) can 112 to shield the SQUID assembly from direct pickup of magnetic fluctuations. The SQUID assembly is located midway between the gradiometers 20L, 20R for maximum symmetry. The gradiometers 20L, 20R are wound on G-10 flanges 114. Winding grooves for source coils 16R, 14R and 16L, 14L are shown in FIG. 8. A wire (not shown) connects the gradiometers to the primary winding of the transformer, housed inside the Nb can 112 containing the SQUID assembly.

Figure 9:
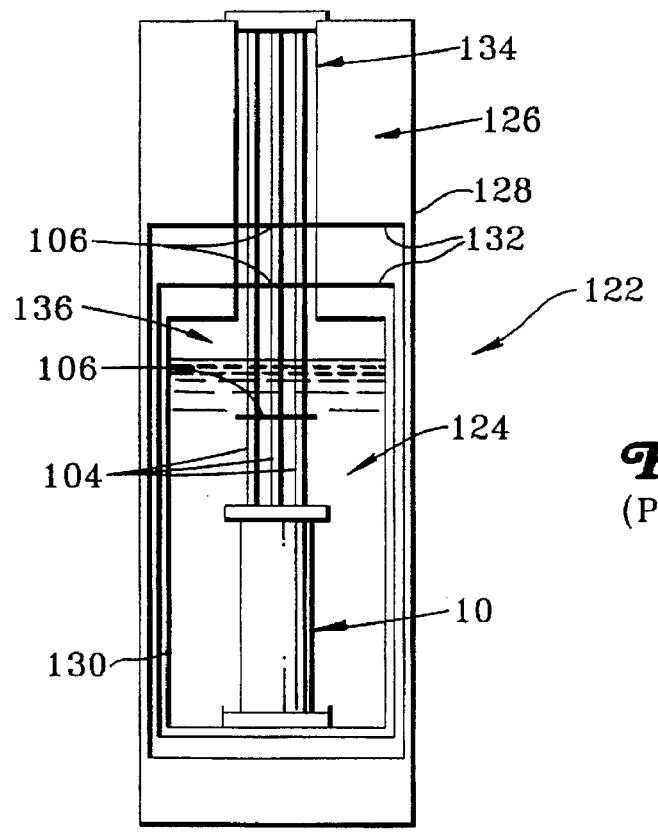
FIG. 9 generally depicts a prior art dewar containing liquid helium in which a magnetic telescope is immersed.

A prior art dewar 122 containing liquid helium 124 in which the magnetic telescope 10 is immersed is depicted in FIG. 9. The rigid assembly of G-10 fiberglass tubes 104 and baffles 106 suspend the magnetic telescope 10 at the bottom of a dewar 122. The G-10 fiberglass tubes 104 and baffles 106 have low thermal conductivity to reduce boiloff of the liquid helium 124.

Important in the development of the magnetic telescope 10 is the reduction in volume and weight of the prior art dewar 122. This must occur while maintaining, or even improving, the cryogenic efficiency of the dewar 122. Reducing the volume and weight of the dewar 122 makes the magnetic telescope 10 more portable for surveys of underground pipeline integrity. Improving cryogenic efficiency of the magnetic telescope 10 reduces the rate at which the liquid helium 124 evaporates (or boils-off), which consequently increase the cost of the survey. For example, since the cost of the liquid helium 124 fluctuates around $6.00 per liter, a loss of 10 liters per day adds a cost of approximately $6.00 per hour to the cost of the survey.

The dewar 122 has an evacuated space 126 between the outer wall 128, at ambient temperature, and the inner vessel 130, at the boiling point of the liquid helium 124. The evacuated space 126 is implemented to insulate the liquid helium 124 which in turn reduces heat carried by the dewar 122. Thermal shields 132 in the evacuated space 126 intercept radiated thermal energy.

Helium boils at a temperature of 4.2 K, at standard atmospheric pressure. In contrast to nitrogen, its latent heat of vaporization (2.6 J/cm$^3$ of liquid) is approximately 700 times smaller than the change in enthalpy of the vapor as it warms from 4.2 K to room temperature. Hence, modern dewar designs, such as the prior art dewar 122, utilize the helium vapor's heat capacity to intercept the heat from the thermal shields 132 before it reaches the liquid.

Referring back to FIG. 9, the thermal shields 132 in the evacuated space 126 connect mechanically to a long, narrow neck tube 134. As it rises, the vapor absorbs heat from the thermal shields 132, by conduction, through a wall of the neck tube 134. In this prior art dewar 122, efficiency is maximized by increasing the aspect ratio of the neck tube 134 (length divided by diameter) and by making the wall of the neck tube 134 as thin as practical. This results in a total volume of the dewar 122 far greater than the volume of the reservoir 136. The prior art dewar 122 of FIG. 9 occupies a volume of 106.6 liters, only 33.5 liters of which is at 4.2 K. The prior art dewar 122 is bulky when housing a conveniently portable magnetic telescope 10, and also loses between 3 and 4 liters of cryogen per day with the magnetic telescope 10 mounted therein. To make the prior art dewar 122 of FIG. 9 compact would require a reduction of the aspect ratio of the neck tube 134, resulting in an increase in the heat impinging on the liquid helium 124, and an increase in cryogen loss rate, all of which would significantly drive up the cost of a survey.

Figure 10:
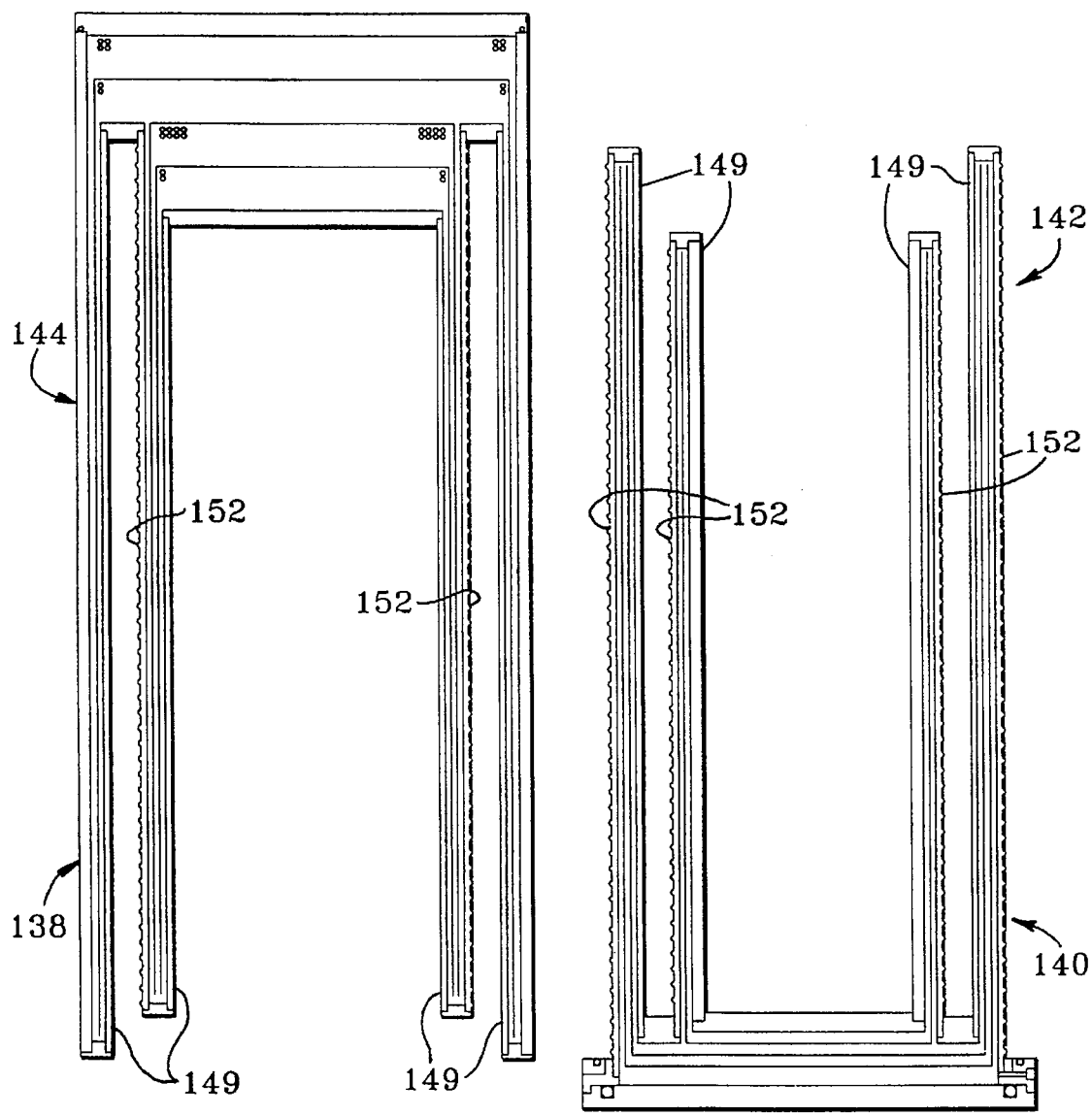
FIG. 10 generally depicts top and bottom halves of a compact dewar featuring a re-entrant neck tube made in accordance with the invention.
Figure 11:
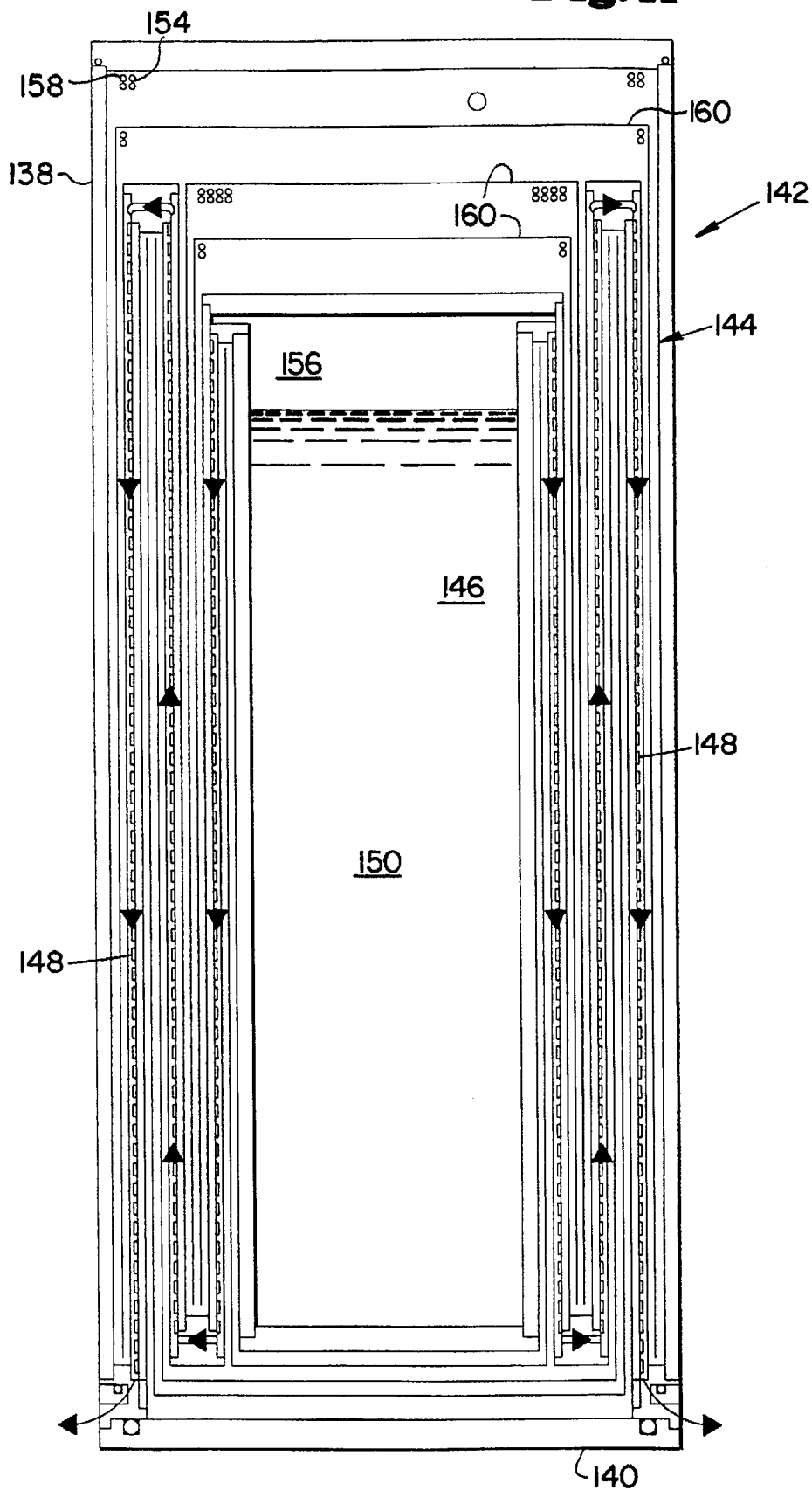
FIG. 11 generally depicts the top and bottom halves of the compact dewar of FIG. 10 mated.

The top half 138 and the bottom half 140 of a compact dewar 142, featuring a re-entrant neck tube 144, is depicted in FIG. 10 in accordance with the invention. The compact dewar 142 reduces the wasted volume of conventional vessels by implementing two separable parts which essentially act like mating double-walled buckets. When the top half 138 and the bottom half 140 slide together, the vapor from liquid helium 146 escapes through a long, spiral groove 148 as best seen in FIG. 11. The spiral groove 148 is machined in mating surfaces of the walls 149. The design effectively collapses the conventional neck tube into a "re-entrant" neck tube 144, offering a very high aspect ratio and low boiloff in accordance with the invention.

In the preferred embodiment, the compact dewar 142 has an overall volume of 7.7 liters compared to 106.6 liters for the prior art dewar 122 depicted in FIG. 9. Important, however, is that the volume factor (ratio of reservoir volume to total dewar volume) is lower. In the preferred embodiment, due to the long, spiral groove 148 which keeps heat from thermal conduction low, projected boiloff is less than 0.5 liters per day. This results in a 15 day working time for a full reservoir 150 of liquid helium 146. The crenelated surfaces 152, best seen in FIG. 10, form the spiral groove 148.

Referring back to FIG. 11, the magnetic telescope 10 is rigidly mounted inside the cryogenic space of the compact dewar 142 before cooling. The top half 138 and the bottom half 140 are mated and the transfer of the liquid helium 146 (and thus cool-down) proceeds. The liquid helium 146 is input into the reservoir 150 via the vent 154. The vent 154 is sealed during normal operation. A tube (not shown) transfers the liquid helium 146. An electrical feedthrough 158 for wiring of the SQUID 70 is also depicted in FIG. 11. The vent 154, the tube 156 and the feedthrough 158 are each long spirals which are thermally grounded to the thermal shields 160 to minimize conducted heat reaching the liquid helium 146.

Figure 12:
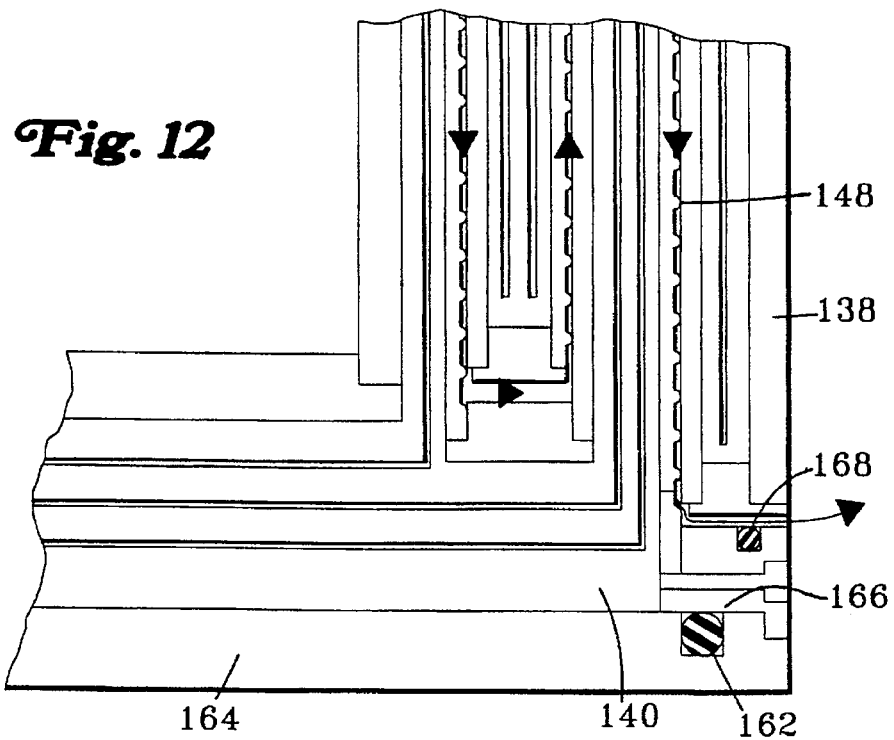
FIG. 12 generally depicts a detail of the lower right-hand corner of the mated compact dewar of FIG. 11, particularly showing the mating between halves in accordance with the invention.

A detail of the lower right-hand corner of the compact dewar 142 of FIG. 11, particularly showing the mating between halves in accordance with the invention, is depicted in FIG. 12. The spiral groove 148 can also be seen. An O-ring 162 maintains the vacuum seal between the end plate 164 and the walls 166 of the bottom half 140 of the compact dewar 142. Another O-ring 168, smaller in diameter than the O-ring 162, holds the top half 138 apart from the bottom half 140 to allow vapor from the liquid helium 146 to escape from the spiral groove 148. The O-ring 168 is notched (not shown) to allow the vapor to escape at only one point on the circumference of the O-ring 168.

As one of ordinary skill in the art will appreciate, modifications and variations may be made to the magnetic telescope herein described which has enhance noise suppression without departing from the scope and spirit of the invention. Various features of the present invention as described in relation to the various embodiments are set forth in the following claims. The disclosure is intended to cover, by the appended claims, all such modifications and variations that fall within the scope of the claims.

I claim:

1. A magnetic telescope having enhanced noise suppression, the magnetic telescope utilized for detecting ferrous metal discontinuities through an overburden, the magnetic telescope comprising:

means for transmitting a first signal through the overburden to the discontinuity, said means for transmitting having at least two pairs of spaced source coils;

said at least two source coil pairs each having an outer coil which substantially encompasses an inner coil, said outer and inner coils having substantially the same axis;

means, substantially located within said means for transmitting said first signal, for receiving a second signal induced by the first signal, but having noise thereon, said means for receiving being substantially located within said inner coils near the axis, said means for receiving including at least two gradiometers, each of said gradiometers having a coplanar pair of oppositely wound semicircles with a substantially common diameter; and means for electronically suppressing said noise in the second signal, said noise suppressing means including means for adjusting a characteristic of said second signal to suppress noise in the second signal, said means for adjusting a characteristic of said second signal having means for adjusting said second signal by using a feedback current in said noise suppressing means and related to said noise of said second signal, said noise suppressing means further having circuitry for substantially cancelling said first signal near the axis.

2. The magnetic telescope of claim 1 wherein said noise suppressing means further comprises means for adjusting currents between said pairs further comprises means for adjusting to maximize suppression of the noise in the first signal.

3. A magnetic telescope having enhanced noise suppression, the magnetic telescope utilized for detecting ferrous metal discontinuities through an overburden, the magnetic telescope comprising:

at least two pair of source coils, said source coil pairs transmitting a first signal through the overburden to the discontinuity;

at least two receiving coils substantially located within said source coils, said receiving coils receiving a second signal induced by the first signal, but having noise thereon, said receiving coils including at least two gradiometers, each of said gradiometers having a coplanar pair of oppositely wound semicircles with a substantially common diameter; and an electronic circuit for balancing the magnetic telescope to suppress said noise in the second signal by feeding back current in said electronic circuit to said second signal.

4. The magnetic telescope of claim 3 wherein said at least two source coil pairs each comprise an outer coil which substantially encompasses an inner coil, said outer and inner coils having substantially the same axis.

5. The magnetic telescope of claim 3 wherein said electronic circuit further includes circuitry for adjusting currents in said coil pairs to maximize suppression of the noise in the first signal.

6. The magnetic telescope of claim 5 wherein said electronic circuit further comprises circuitry for adjusting a characteristic of said second signal to maximize suppression of the noise in the second signal.

7. The magnetic telescope of claim 6 wherein said electronic circuit further comprises means for adjusting a current of said second signal by using a feedback current related to said noise of said second signal.

8. A magnetic telescope having enhanced noise suppression, the magnetic telescope having use in detecting a discontinuity in an underground article, the magnetic telescope comprising:

two pairs of source coils, each said source coil pair having an outer coil and an inner coil for producing a magnetic flux to illuminate the article, wherein said outer and inner coils produce magnetic flux capable of producing a minimal magnetic flux at known locations in the telescope;

a pair of gradiometers located substantially at said known locations, for picking-up magnetic flux appearing to originate from the discontinuity in the article;

an electric circuit coupled to said gradiometers for detecting the magnetic flux, achieving noise suppression by feeding back magnetic flux from said electric circuit to said detecting means in an amount which suppresses the noise, and identifying the discontinuity.

9. The magnetic telescope of claim 8 wherein said outer and inner coils are arranged in a differential configuration.

10. The magnetic telescope of claim 9 wherein said known location further comprises an axis about which said inner coil and said outer coils are centered.

11. The magnetic telescope of claim 8 wherein said means for detecting the magnetic flux further comprises a superconducting quantum interference device (SQUID).

* * * * *

UNITED STATES PATENT AND TRADEMARK OFFICE
CERTIFICATE OF CORRECTION

PATENT NO. : 5,633,583
DATED : May 27, 1997
INVENTOR(S) : Podney

It is certified that error appears in the above-indentified patent and that said Letters Patent is hereby corrected as shown below:

Column 7, line 15, delete "$\phi_r$," and insert --$\phi_I$--.

Column 7, line 17, delete "$\phi_r$," and insert --$\phi_I$--.

Column 7, line 21, delete "$\phi_r$," and insert --$\phi_I$--.

Column 8, line 60, delete "$+\sigma\delta\vec{A}\cdot\vec{B}_\circ$" and insert --$+\delta\vec{A}\cdot\vec{B}_\circ$--.

Column 8, line 62, delete "$+\sigma\delta\vec{A}$" and insert --$\delta\vec{A}$--.

Signed and Sealed this

Sixteenth Day of June, 1998

*Attest:*

*Attesting Officer*

BRUCE LEHMAN

*Commissioner of Patents and Trademarks*